(12) United States Patent
Zimmerman

(10) Patent No.: US 7,966,971 B2
(45) Date of Patent: Jun. 28, 2011

(54) METHOD AND SYSTEM FOR MONITORING AND REDUCING RUMINANT METHANE PRODUCTION

(75) Inventor: Patrick R. Zimmerman, Rapid City, SD (US)

(73) Assignee: C-Lock Inc., Rapid City, SD (US)

( * ) Notice: Subject to any disclaimer, the term of this patent is extended or adjusted under 35 U.S.C. 154(b) by 197 days.

(21) Appl. No.: 12/469,882

(22) Filed: May 21, 2009

(65) Prior Publication Data

US 2009/0288606 A1 Nov. 26, 2009

Related U.S. Application Data

(60) Provisional application No. 61/055,933, filed on May 23, 2008, provisional application No. 61/209,179, filed on Mar. 4, 2009.

(51) Int. Cl.
*A01K 5/00* (2006.01)
*A01K 29/00* (2006.01)
(52) U.S. Cl. ..................... 119/51.02; 119/174
(58) Field of Classification Search ............... 119/51.02, 119/174, 417, 418, 421
See application file for complete search history.

(56) References Cited

U.S. PATENT DOCUMENTS

| | | | | |
|---|---|---|---|---|
| 4,830,010 A | * | 5/1989 | Marshall | 600/300 |
| 5,265,618 A | * | 11/1993 | Zimmerman | 600/531 |
| 6,270,462 B1 | * | 8/2001 | Mottram et al. | 600/529 |
| 6,488,635 B1 | * | 12/2002 | Mottram | 600/551 |
| 7,350,481 B2 | * | 4/2008 | Bar-Shalom | 119/859 |

FOREIGN PATENT DOCUMENTS

| | | |
|---|---|---|
| KR | 20060019062 A1 | 3/2006 |
| WO | 0126482 A1 | 4/2001 |
| WO | 2004072801 A2 | 8/2004 |
| WO | WO2009/013002 A2 * | 1/2009 |

OTHER PUBLICATIONS

International Serach Report, PCT/US2009/044990, mailed Jan. 19, 2010.

* cited by examiner

*Primary Examiner* — Yvonne R. Abbott
(74) *Attorney, Agent, or Firm* — Marsh Fischmann & Breyfogle LLP; Kent A. Lembke

(57) ABSTRACT

A method, and systems implementing such method, for reducing methane emissions by ruminants. The method includes providing a feed dispenser for feeding ruminants one or more nutrient supplements, and the feed dispenser includes a gas analyzer proximate to where the ruminant places its head. The method includes determining a particular ruminant has accessed the feed dispenser such as by reading an identifier from an RFID ear tag and operating the feed dispenser to provide a ration of methane-controlling nutrient supplement. The method includes using the gas analyzer to determine levels of carbon dioxide and methane and operating a data analyzing station to determine a ratio of methane to carbon dioxide and modify the type or amount of nutrient supplement for the ruminant for a next feeding to control methane production or achieve an animal production goal, such as by selectively operating a hopper with two or more supplements compartments.

24 Claims, 6 Drawing Sheets

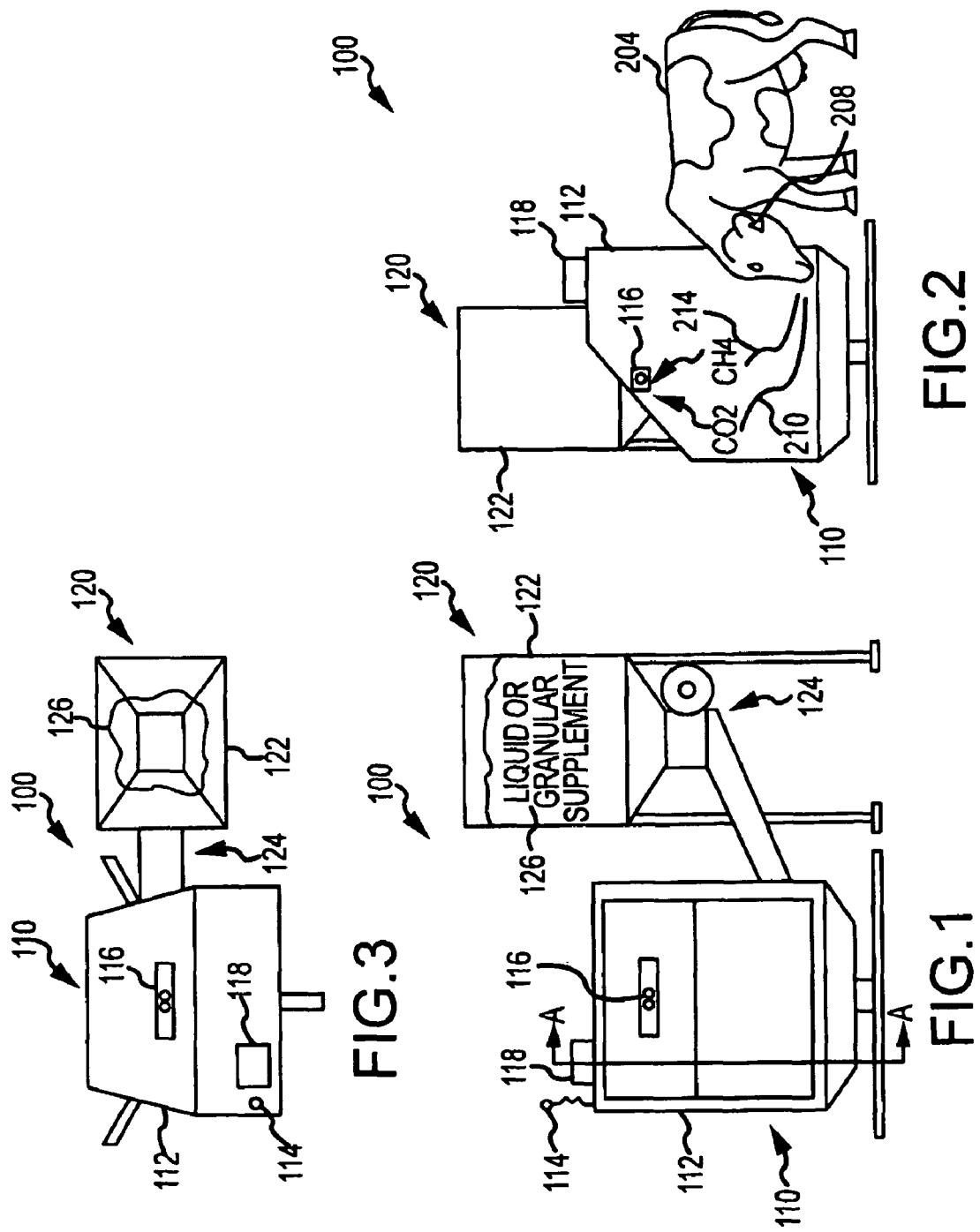

METHOD AND SYSTEM FOR MONITORING AND REDUCING RUMINANT METHANE PRODUCTION

CROSS-REFERENCE TO RELATED APPLICATIONS

This application claims the benefit of U.S. Provisional Application No. 61/055,933 filed May 23, 2008 and of U.S. Provisional Application No. 61/209,179 filed Mar. 4, 2009, both of which are incorporated herein by reference in their entireties.

FIELD OF THE INVENTION

The present invention relates to methods of monitoring gaseous emissions of ruminants and of utilizing the information to reduce ruminant methane emissions and to increase ruminant production efficiency.

BACKGROUND OF THE INVENTION

Methane is a significant greenhouse gas. One ton of methane is equivalent to approximately 21 to 22 tons of carbon dioxide with respect to its global warming potential. As a result, the reduction of one ton of methane emissions can be considered as achieving a reduction of 21 or more tons of carbon dioxide and can generate about 21 tons of carbon credits (as carbon dioxide) in the evolving Greenhouse Gas (GHG) market. Moreover, methane has about a 12 year half life in the atmosphere and is increasing worldwide at an annual rate of around one half of one percent (0.5%) per year. Accordingly, reduction of presently excessive methane emissions into the atmosphere is most desirable.

The emission of greenhouse gases (GHG) including methane from bovines and other ruminants is believed to be a significant contributor to global warming. Some scientists estimate that livestock contributes up to thirty-seven percent (37%) of the total global methane ($CH_4$) budget. Methane emission from bovine sources, of which the majority is through belching, can be significantly reduced through modification of cattle diet. Attempts at reduction typically involve using nutrient blocks or other feed supplements while other efforts have concentrated on modification of the genetic composition of the animal herd. To date, efforts to measure and potentially remediate this source of GHG from ruminants have not been considered feasible or widely implemented in part because of high costs related to monitoring $CH_4$ emission from ruminants in coordination or concurrently with measurement of supplement use.

Ruminants produce significant amounts of methane during their digestive processes. The multi-stage digestion system in ruminants contains substantial microbial consortia, which through anaerobic digestion breaks down food components to create low molecular weight fatty acids, alcohols, and microbial protein that travel through the gut and become reabsorbed. Methane emissions are a consequence of this process and constitute an energetic loss equivalent of from a third of a pound to potentially one half a pound of potential weight gain per head of beef cattle per day. Energetic losses from particular ruminants such as dairy cows are likely even higher than these estimates. Carbon dioxide and methane produced in the rumen is eructated or belched through the animal's nostrils and mouth. On average an animal belches about every 40 seconds. In addition to methane release causing GHG concerns, the production of methane by ruminants and its loss through eructation represents a significant energy loss to ruminant animal production efficiency. As diet quality decreases, methane emissions as a fraction of gross energy intake rises and dietary efficiency decreases. Therefore, the ability to monitor changes in the production of methane from ruminants provides a tool to monitor and diagnose digestion efficiency as well as to monitor levels of GHG emissions. Some recent studies have indicated that methane production is a function of animal genetics, animal diet and other factors that affect rumen microbial flora. The ability to easily monitor changes in methane production under field conditions represents a significant improvement in animal management capabilities.

The loss of methane is a significant energy loss to the animal. Globally this is equivalent to trillions of dollars of lost dietary efficiency. Animal nutritionists know that the metabolic pathways in the rumen can be modified by diet to reduce methane production and to more efficiently process feed. Several dietary supplements are available, and, in many cases, the cost of the nutrient supplement is easily exceeded by the animal weight gains, making use of supplements attractive to ruminant producers such as the cattle industry. Accordingly, reduction in methane emissions by ruminants can help animals become more productive per unit of forage or feed while also reducing undesirable methane emissions. When animals eat low quality forage, it actually takes a longer time to pass through their gut. Hence, the poorer the quality of forage, the longer it takes the animals to digest the forage, and this results in lower weight gain but more methane production. However, since monitoring of changes in methane performance under actual field conditions has been difficult or impossible to achieve in the past, it is not practical to modify forage composition to minimize methane losses nor to monitor and modify genetic factors that influence ruminant methane production. A system that can monitor changes in relative methane emissions could therefore provide important information to ruminant producers concerning optimal forage and grazing conditions. In addition, since animals fed a highly energetic diet process that feed more quickly, they produce more methane per unit time, but much less methane per unit of production of meat or milk. Therefore it can also be important to measure methane and carbon dioxide from the rumen as well as carbon dioxide from the animal's breath in order to differentiate rumen processes from catabolic and respiratory processes and to measure their emissions relative to measurements of animal production—such as animal weight gain and/or animal milk production.

U.S. Pat. No. 5,265,618 discloses a system that measures the flux of metabolic gas emissions from cattle or other animals. The system does not require that the animals be confined to a chamber or stall. An animal whose metabolic gas emissions are to be measured is first fed a permeation tube (i.e., a metal tube with a gas-permeable plastic disk in one end). Inside the tube is a tracer that is physiologically inert. The permeation tube is filled with pressurized liquid tracer, which slowly permeates in gaseous form through the plastic disk. In order to measure rumen-produced and respiratory metabolic gases, a sample container, such as an evacuated container or an inflatable collar, is placed on the animal. A small diameter sample tube is attached from the sample container to a halter and terminates somewhere near the animal's mouth. When the animal breathes, it exhales metabolic gases as well as the tracer. A sample of air containing both the metabolic gases and the tracer gas is then collected through the sample tube. Since the permeation rate of the tracer is known and constant, the ratio of the flux of a given metabolic gas to the flux of the tracer gas is equal to the ratio of the mixing ratios of the respective gases in the air sample that is collected. The rate of flux of metabolic gas from the animal's rumen is thus readily calculated by measuring the metabolic gas and tracer mixing ratios in the sample thus collected. This system, however, requires substantial animal handling and training to be effective. Moreover, it is not practical for animals that do not tolerate a halter, which may include large percentages of a ruminant herd. Also the system can only provide time-integrated values that represent average rumen, catabolic and respiratory processes. The system can not be used to track short-term changes nor can it isolate rumen processes from respiratory processes related to catabolism.

Schemes to convert increased ruminant metabolic efficiency into marketable GHG offsets have not been financially viable. Though mineral blocks, other effective nutrient supplements, and rumen-modifying antibiotics and ionophores are effective in reducing methane production and in many cases cost only a few cents per day, at the current value of greenhouse gas (GHG) offsets, compliance, documentation, and monitoring costs exceed the value of the GHG offsets that can be generated. Also, animals fed poor-quality forage have lower methane emission rates per unit time than animals fed high quality diets. However the emission of methane as a function of gross energy intake is much higher for an animal fed low quality forage compared to an animal fed a high quality diet. As a result methane per unit of animal production is much higher for low-quality, poorly digested forages compared to animals fed a high quality digestible diet. Specific nutrients, missing from low quality forage can be supplemented through the use of nutrient feeders to boost digestibility, resulting in increased efficiency and lower methane emissions per unit of animal production. It is therefore desirable to document relative changes in methane emission rates and it is not always necessary to measure fluxes of methane per unit of time. That is changes in ratios of methane compared to carbon dioxide for respiration as well as for rumen gas per unit of production can provide the information required to document animal performance improvements that lead to quantifiable methane reductions and can generate carbon credits. In addition, measurement of emissions of methane and carbon dioxide from the rumen and differentiation of this flux from measurements of carbon dioxide resulting from catabolism over shorter time periods are necessary in order to track energy flows through a specific ruminant and to document the efficiency of production of meat and milk in a way that facilitates interactive treatment to improve productive efficiency and lower methane emissions per unit of production.

SUMMARY OF TIE INVENTION

One or more embodiments of the invention provide an implementation of a field station that can monitor methane emissions and/or emissions of carbon dioxide. Changes in the ratios of methane compared to carbon dioxide may be used to indicate changes in metabolic efficiency, and these determined emissions, ratios, and changes in metabolic efficiencies may then be tracked in some embodiments with this data stored on an individual animal and/or herd basis in system's memory or data storage. Further, this data can be routed to a computer where numerical models or other calculations may be performed (e.g., with software programs or modules run by the computer) to transform the data into methane fluxes. In addition, either an internal (e.g., from the animal) or an external (e.g., from an external source) tracer can be incorporated into the system. In this case, halters or other devices may not be used, and the animals may not be handled or confined while methane and carbon dioxide fluxes may be directly measured from each animal.

For example, in one exemplary but not limiting embodiment of the present invention, a ruminant's gaseous emissions are monitored, methane emissions are determined, and the ruminant's feed supply is adjusted or supplemented or the ruminant is otherwise treated to reduce methane emissions. In some embodiments, a non-dispersive infrared instrument monitors carbon dioxide and methane emitted by a ruminant. Alternatively, methane and carbon dioxide emission measurements are obtained using methods such as tunable diode laser absorption spectroscopy (TDLAS), open-path Fourier transform infrared spectroscopy (FTIR), other infrared-based methods, miniaturized gas chromatography/flame ionization detection (GC/FID), or miniaturized mass spectrometry or it can even be determined through the collection of periodic gas samples subject to later analysis using gas chromatography.

The information thus obtained may be considered by software programs/modules run by one or more computers/processors in the system along with animal statistics available from a database stored in system memory or otherwise accessible (e.g., via wired or wireless connections to a digital communications network such as the Internet or an intranet or the like) and/or from information associated with an RFID tag attached to the ruminant, which may include heritage information, e.g., whether the animal is weaned, its age, its internal body temperature, its weight and other physiological parameters, and the like (e.g., the RFID tag may have readable memory or may provide an identifier that can be used to retrieve this information from system, or otherwise available/accessible, data storage or memory). Alternative methods for identification of individual animals may include eye/retinal patterns, laser-imprinted bar codes or alphanumeric codes, facial pattern recognition, gases or chemical compounds emitted in the breath or from other parts of the animal, and genetic information. Based upon the emission information and the other information about the ruminant, one or more of the software programs or modules determines a supplement prescription or mix (e.g., particular supplements and amounts of each chosen supplement). The system may then be operated such that one of a plurality of supplements and/or a particular amount of a supplement or of a plurality of supplements is offered to the ruminant by operation of a feeding station (e.g., control signals transmitted by the controller/operator of the methane monitoring and reduction system to supplement/feed dispensing devices of the feeding station).

In a method of an exemplary embodiment of the present invention, a ruminant presents itself at a feeding station at which carbon dioxide and methane emitted by the ruminant in its breath are measured. Other measurements may also be taken and routed into the data logger. These data can be provided by individual sensors and stored in a ruminant and methane monitoring database. In other cases, these data may be derived from signals read from the animal's RFID ear tag and read into the data logger. In some embodiments, at least one determination is made about the production of methane by the animal (e.g., by a methane monitoring module run by the computer/processor to determine methane emissions/production and/or to process methane and carbon dioxide emission ratios to determine a current metabolic efficiency for the animal). Additional determinations which may be made including the identification of one or more supplements or a mixture of supplements and an amount or amounts thereof to offer to the ruminant to reduce the determined methane emission which would be expected to subsequently occur should the ruminant's diet not be modified.

According to one aspect, a ruminant methane feed station may be constructed and instrumented to function in several modes. In one example, the feed station includes a hood to restrict the effects of the wind and/or to serve to concentrate the breath of the animal. In this case, an animal, such as a cow, would insert its head into an opening. At that time, a sensor may be used to read an ear tag (e.g., a tag including an RFID chip or tag) to determine the age and type of animal. Based on this information, a specific nutrient mix could be released by selective operation of feed dispensers at the feed station. In one useful embodiment, the mixture is designed to reduce the production of methane by the ruminant. The determinations controlling the type and amount of nutrient performed by software modules run by the computer(s) of the system may be based on input from sensors mounted inside the feed station and on the ground in proximity to the feed station. Information collected could include animal weight in order to determine animal weight gain, methane and carbon dioxide emission ratios while at/near the feed station to determine animal metabolic efficiency, and/or additional measurements as useful to document performance and to generate CERCs (Carbon Emission Reduction Credits).

In another example, in addition to the measurement of methane and carbon dioxide ratios in the animal's breath, the insertion of the animal's head into a feed hood, stall, or feed station triggers the release of a specific, controlled flow-rate tracer. The tracer is preferably in some embodiments an inert gas such as sulfur hexafluoride, butane, or other chemical compound that is measured with instrumentation installed in the feed station. The dilution of the tracer is used to correct methane and carbon dioxide measurements for the effects of atmospheric dilution. In this way, the flux of methane and carbon dioxide can be determined in addition to the metabolic methane and carbon dioxide ratios.

In another example or embodiment, the animal's breath is used as a tracer of atmospheric dilution. Because the breath of a ruminant is saturated with water, changes in water vapor measured by a specific sensor provided at the feed station are sometimes used to document mixing. Alternatively, mixing could be determined by monitoring other gases or compounds naturally occurring in ruminant breath such as low molecular weight alcohols and organic acids. From this information, absolute fluxes of methane could be measured/determined by software/hardware provided in an embodiment of the ruminant monitoring system. In another embodiment, diurnal cycles of rumination are captured by locking animals out of the feeder until specific times of the day. For example, an animal might typically approach the GreenFeed system or feeding station at a specific time of day. The system could be programmed/controlled so that no supplement was provided unless the animal approached at a different time. In this case, a visual or audio stimulus is sometimes provided by the GreenFeed system when it is "Live" to dispense the nutrient supplement (or attractant feed). The system is therefore programmed to capture ruminant processes at differing times throughout the diurnal cycle and therefore define/determine methane flux behavior. In another embodiment, the system is programmed so that specific individuals are dispensed supplements on alternate time-period schedules and only a placebo during other time periods. In this way, the changes in methane emissions associated with the application of a specific treatment are more unequivocally determined and stored in memory or in the monitoring/tracking database (e.g., documented).

In a further embodiment, a nutrient block system is provided to monitor methane and carbon dioxide concentrations of tidal breath as well as the eructation of ruminant animals while they are in a pasture. The feed station or system portion of the monitoring system looks similar to a hooded salt-lick mounted on a short post. The nutrient block may be surrounded on all but one side by a cover. The uncovered side has hole large enough for an animal to insert its head and access a nutrient block or container(s) of one or more nutrients. Mounted under the hood is an RFID tag reader for activating and reading/receiving information about each animal from its RFID ear tag. The nutrient-block station may further include a methane/carbon dioxide monitor, a data logger, and/or a communication device (e.g., a Bluetooth transmitter, a cell phone with a modem, or the like). The station may in some cases contain a global positioning satellite (GPS) chip to obtain and collect information about location of the unit and the time of day that it was accessed by the animal. Again, this information may be stored by the datalogger at the feeding station or at a differing data storage device, such as a centralized datastore used to store a database collected from a plurality of such feeding stations and/or for a set of animals or a monitored herd of ruminants. In some cases, the system is powered by batteries recharged by solar cells, although other power sources may readily be used.

In one operating method for a methane monitoring and production control system, when an animal approaches the nutrient block station of an embodiment of the present invention, the system turns on for a specified time-period to monitor and document methane/carbon dioxide ratios, the animal's identification number (such as read from an RFID-based ear tag), the time (from a system clock at the feeding station), and/or the location of the station (from a feeding station identifier and look up, from a GPS chip, or the like). Based on information collected and obtained and based on determinations made based on the information by system software, a supplement is made available via selective operation of feed dispensers at the feeding station to the animal to control, reduce, or maintain methane emissions at a presently desired level (e.g., a goal methane emission level may be stored in system memory for each animal in a monitored herd and the system may compare a currently determined emission rate with the goal level to determine whether one or more supplements should be provided and in what amounts to increase, decrease, or maintain methane emission levels for the feeding animal). In some cases, it is likely the animals will consume one to two ounces of supplement per day, and the amount of supplement consumed per animal may be controlled by modifying the salt content of the supplement (e.g., not only prescribing/controlling supplements and their amounts but also controlling additives provided with such a supplement mix to encourage the supplement(s) to be consumed).

In practice, the station may be placed strategically in a field near a point of congregation such as a water source with a typical feeding station serving a relatively large number of animals such as a station serving 40 to 100 animals. The system may be loaded with a placebo mineral block to document the baseline methane emissions for the herd and the pasture. In this way, the mineral supplement may be added to document GHG reductions, so that each animal, as well as the whole herd, may be monitored in a very cost-effective way. If exact or more accurate emission rates of methane and carbon dioxide are found useful (e.g., instead of relative changes in metabolic efficiency), an optional tracer release system can be incorporated into the system. The tracer release system utilizes a third chemical species (e.g., butane or an inert fluorocarbon that would be emitted at a defined rate). The dilution of the tracer is then utilized to correct for limited atmospheric mixing that may occur when the animal's head is "under the hood." This may not be used in some implementations, though, since concentrations of methane and carbon dioxide under the hood will likely be many times greater than ambient concentrations and efficiency gains can be documented with the ratio of the two gases without the absolute emission rate.

In addition to the generation of high value GHG offsets, the system may serve as a livestock management tool. The methane/carbon dioxide ratios obtained provide valuable information about the condition of the animal and of the pasture. Methane and carbon dioxide concentrations under the hood of the mineral block monitoring system when an animal is present are normally fairly high, i.e., much above ambient, so that measurements of metabolic gas concentrations are facilitated. If preferred, however, an embodiment of the system can employ an OEM NDIR instrument if necessary. Although the cost of this type of sensor can reach several thousand U.S. dollars, the GreenFeed station or feeding station is still likely to be cost-effective. Since the station is automated, the monitoring costs per animal will be quite low. Because one station can be shared among many cattle, the cost per animal is also relatively low.

BRIEF DESCRIPTION OF THE DRAWINGS

FIGS. 1-3 illustrate front, sectional, and top views, respectively, of one embodiment of a system for monitoring and controlling ruminant methane production/emission (or a GreenFeed system);

DETAILED DESCRIPTION OF PREFERRED EMBODIMENTS

Figure 4:
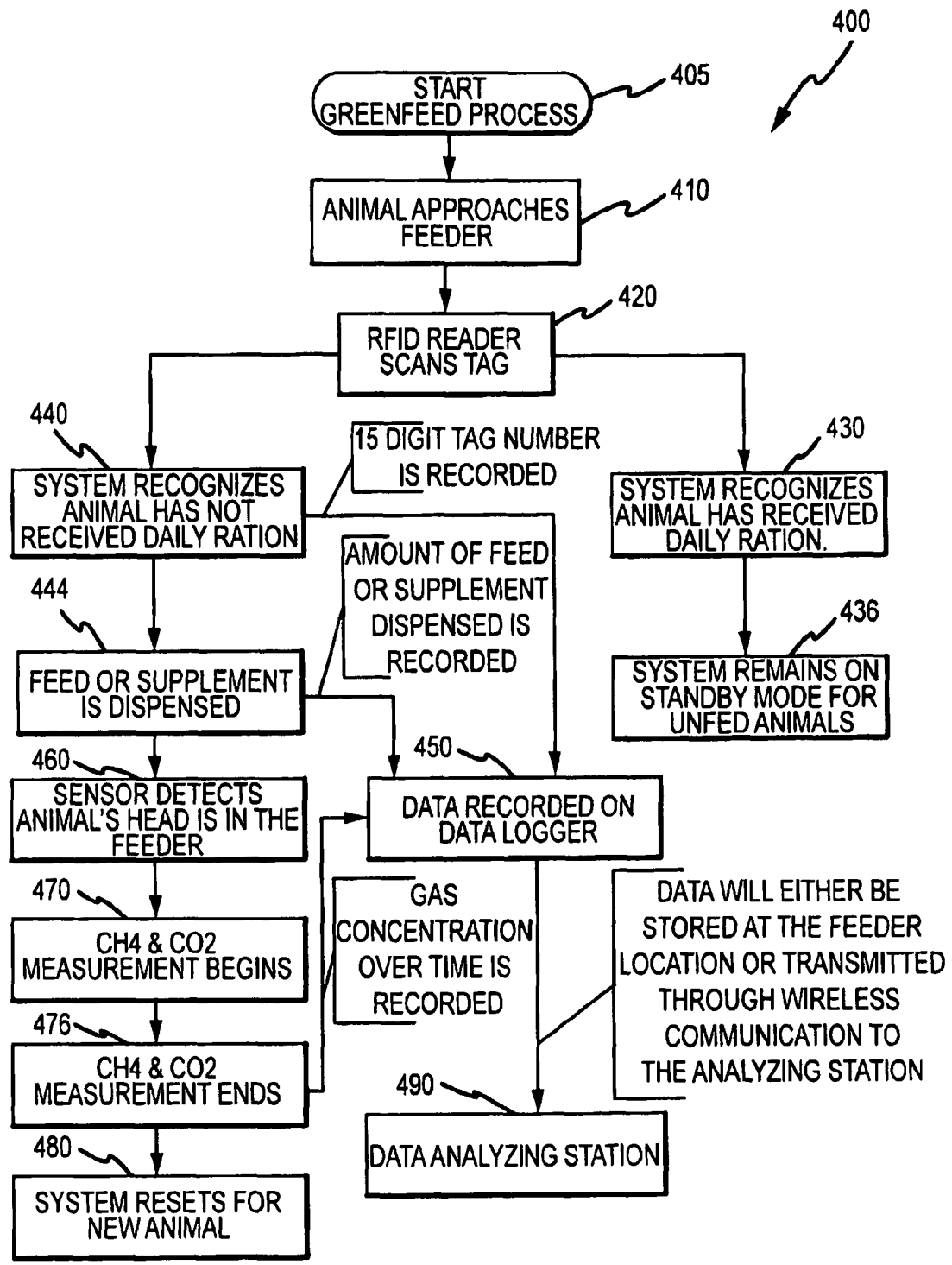
FIG. 4 illustrates a method of monitoring and controlling ruminant methane production and/or emission such as may be implemented, wholly or in part, by operation of the system shown in FIGS. 1-3.

The methods and systems described herein are expected to substantially reduce the parasitic GHG emissions from livestock and increase grazing efficiency. These techniques for monitoring and reducing/controlling ruminant methane production are further expected to have substantial economic potential. In addition to animal efficiency gains, actual methane emission reductions expected based on the wide range of literature values may, for example, produce GHG offsets worth from $1 to $20 (US dollars) per animal per year depending on diet and animal genetics.

FIGS. 1-3 illustrate exemplary components of one embodiment of a system 100 for monitoring and controlling ruminant methane production/emission. The illustrated system 100 may incorporate a ruminant ear tag reader 114 (e.g., a reader adapted for reading an RFID tag 208 placed on an ear of an animal 204) so that animals 204 with ear tags 208 can approach the station 110 and be identified with the shown RFID reader 114 that provides data to the data logger 118, with the reader 114 and data logger 118 being mounted on the hood/manger 112 of the station 110 in this example system 100. The GreenFeed system 100 (with "GreenFeed" system being used interchangeably herein with labels such as system for monitoring and controlling ruminant methane production/emission and the like) is in some cases designed to dispense custom formulations into the manger 112 for each specific animal 204 by selectively controlling/operating one or more feed system 120 or its dispensers/hoppers 122 with feed/chute control mechanisms/assembly 124.

For example, the dispenser/hopper 122 may include liquid or granular supplement 126 and may be selectively operated. This hopper 122 may have one or more compartments (with only one shown for ease of illustration but not limitation) each containing one or more differing supplements 126, and these compartments may be separately operated by the output mechanisms 124 of the automated nutrient dispenser 120 in response to methane and carbon dioxide emission determinations (such as by the illustrated $CH_4$ and $CO_2$ analyzer 116 that may process releases 210, 214 of $CO_2$ and $CH_4$ within the hood/manger 112 and provide data or control signals to the automated nutrient dispenser 120 and, in some cases, determinations of present/real time metabolic efficiency of the feeding animal 204. The system 100 (or its software programs or modules not shown but run by one or more onboard/local processors or remotely located processors) may also make decisions based on measurements of animal temperature (e.g., measured by way of a sensor placed inside the animal's ear canal (not shown in FIGS. 1-3)) and/or based on animal metabolic gases measured by the GreenFeed system 100. Numerical computer models resident in a computer module of the system 100 (such as in the analyzer 116, data logger 118, automated nutrient dispenser 120 but not specifically shown) interfaced with the data logger 118 either built into the system 100 or operated remotely.

The following sequence describes exemplary operation of the illustrated GreenFeed system 100 during an animal measurement cycle with at least some of these steps being illustrated in the example flow chart for a GreenFeed process 400 in FIG. 4.

A GreenFeed system, such as system 100, may include: one or several dispensers (such as dispenser 122) for specific feed supplements (such as liquid or granular supplements 126); a monitoring system for metabolic gas emissions from animals (such as NDIR $CH_4$ and $CO_2$ analyzer 116 and data logger 118 of system 100); an RFID reader (such as reader 114) to read data from each animal's ear tag (as shown at 208 in FIG. 2); sensors built into a ground-mounted weight scale to record the approaching animal's weight (not shown in FIGS. 1-3 but may be provided in system 100); solar panels to supply power when main power is not available (not shown in FIGS. 1-3 but also may be included in system 100); and batteries that are recharged by the solar panels residing in a pasture (again, these are not shown in FIGS. 1-3 but are included in some system 100 to practice embodiments of the invention). The process 400 starts at 405 such as by providing the animal feed stations and nutrient dispensers within a pasture or feeding area for ruminants, and step 405 may also include loading processing software/modules in the system to analyze monitored emissions data and, in response, to operate the nutrient dispenser for a particular animal (such as animal 204) or the monitored/controlled herd.

Periodically, the system (such as system 100) turns on and makes measurements of ambient air inside the manger portion of the GreenFeed system (such as the hood/manger 112 of feed station 110 shown in FIGS. 1-3 where the animal 204 inserts its head). These air samples are the background samples, and sampling may be performed by the analyzer 116 or other devices of a system (such as system 100). The GreenFeed system may incorporate optional front and side curtains (not shown in system 100 of FIGS. 1-3) to restrict mixing of ambient air under extremely windy conditions. Alternatively or additionally, the GreenFeed system manger/feeder unit (such as unit 110 of system 100) may be made to pivot so that its opening is always aligned downwind. This will help to restrict atmospheric mixing that could cause dilution of metabolic gas emissions and concentrations.

When an animal approaches at step 410, the system monitors its ear tag with a tag or RFID reader at 420 and such reading may awaken the feeding system. A computer program run by a processor(s) may be provided in the GreenFeed system that monitors the time of day and determines whether or not to dispense a specific feed material based on the time of day and/or the particular animal such as based on the ear tag determination. In some cases a placebo feed, one that attracts the animal but has no significant metabolic effect can be dispensed. The placebo documents the baseline for the performance of the specific animal. As shown, the system may determine at 430 that the animal linked in a database with the read ear tag has received their daily ration, and, if so, the method 400 continues at 436 with the system operating in a standby mode for additional approaching animals, e.g., unfed animals to dispense appropriate nutrients.

After the RFID tag is read at 420, the system (or its monitoring software) may determine at 440 that the animal associated with the read ear tag has not received its daily ration of the methane controlling or other nutrients. In some cases or implementations of process 400, the tag number of the ear tag (e.g., a 15-digit number or the like) may be recorded in the data logger as shown at 450. At 444, based on a lookup in a database for the particular animal, the automated nutrient dispenser may be operated to dispense feed and/or nutrient supplements, and the amount of feed and/or supplements dispensed may be recorded to the data logger or other data storage device in the GreenFeed system as shown at 450.

At 460, a separate sensor/detector associated with the feed station or the RFID reader may trigger the gas and/or other monitoring instrumentation to turn on. The monitors (such as analyzer 116 in system 100) can either be mounted within the GreenFeed hood and/or they can be located remotely, and air samples collected from within the GreenFeed hood and manger can be routed to the analytical instruments. In one implementation, measurements are made as shown at steps 470 and 476 of methane, carbon dioxide, and water vapor such as with the sensor and/or measurement devices shown in FIGS. 1-3. In addition, animal weight, animal milk production, animal core temperature, and other data can be routed to the data logger (such as data logger 118 of system 100) and computer system of the illustrated feeding station of FIGS. 1-3. These data may then be transferred to a computer program or series of programs in which numerical models are run such as within the data analyzing station 490 to result in or produce decisions about the types and amounts of specific antibiotics, and/or nutrient supplements to dispense at step 444 in the next or current feeding of animal or access of a feed station (e.g., provide a particular "prescription" or "diet" of supplements and the like to dispense at this time to this particular animal based, typically, on the methane emissions detected and/or on metabolic efficiency of the animal). The gas concentration over time as measured in steps 470 and 476 may be recorded by data logger as shown at 450 concurrently with or prior to transfer to the nutrient supplement selection program module or programs at data analyzing station 490. The data may either be stored at the feeder location or transmitted through wireless or wired communications to the analyzing station 490.

As shown in method 400, based on the supplement determinations by data analyzing station 490, the GreenFeed system (such as system 100) dispenses the required (or determined useful for controlling methane production) nutrient supplements and/or antibiotics into the manger by operation of the feed dispenser/hopper (e.g., the hopper 122 with liquid or granular supplement 126 to meter out a particular amount of one or more supplements/feeds 126 as shown in FIGS. 1-3).

The analytical measurement system (e.g., analyzer 116, data logger 118, and data analyzing station 490 and the analyzing stations software modules) measures changes in methane and carbon dioxide ratios. When an eructation occurs, methane concentrations will spike. Carbon dioxide from aerobic respiration will tend to increase linearly as the animal breathes while its head is in the restricted space. Since little methane is emitted in an animal's breath, aerobic and anaerobic respiration can be differentiated. FIG. 3 illustrates a typical pattern of ruminant animal breath and eructation cycle. This data can then be compared to data obtained from the baseline case by the data analyzing station 490, for example, for the individual to determine relative changes in methane emission rates. A numerical model (e.g., software module run by station 490) describing animal metabolic functions can then be initialized with this data either on a remote computer or on a resident computer of data analyzing station 490 to calculate greenhouse gas reductions.

The methane monitoring and emission control or GreenFeed system may incorporate a telemetry system to transmit data to a remote computer (or data analyzing station 490 as shown in FIG. 4) where it may be stored in computer memory or data storage (such as in a database with supplement and methane emission data collected at the data logger for each animal) and/or further processed for a plurality of animals and/or stations as shown in FIGS. 1-3. The GreenFeed system may include a resident computer (using a processor(s) to run one or more software programs/modules (not shown) but provided in some embodiments in the data analyzing station 490 to cause the computer(s) or their processor to perform particular functions) to process data and aggregate the collected and logged data to generate a report of emission reductions and performance efficiency for each individual animal. In some embodiments, the system and its data analyzing station may function to aggregate data for individual animals and/or for the entire herd. The GreenFeed system may, in some embodiments, be linked to other systems, such as but not limited to the C-Lock Technology and/or GreenCert™ (U.S. Pat. Nos. 7,457,758 and 7,415,418, which are both incorporated herein in their entirety by reference). In some embodiments providing linkage between the GreenFeed system and other systems the ruminant monitoring and emission control data may be transformed into carbon credits (e.g., C-Lock certified carbon credits or the like) that may be transparent and verifiable.

A tracer release can be incorporated into the GreenFeed system so that a known quantity of an easily-measured trace gas, not generally produced by ruminants is released into the GreenFeed manger area (e.g., into the hood 112 of feed station 110 in system 100 of FIGS. 1-3 for measurement by analyzer 116 or a separate trace gas analyzer). Exemplary tracers include butane, propane, ethane, sulfur hexafluoride and/or many other compounds that are typically readily available and easy to measure. Measurements of the decay of this tracer gas may be used to calculate dilution from mixing with ambient air. Alternatively, the tracer release can be continuous over a long enough time-period so that the steady-state concentration can be used to estimate dilution of the metabolic gas emissions from animals (by the analyzer 116 or data analyzing station 490 and its software/processing modules).

Figure 5:
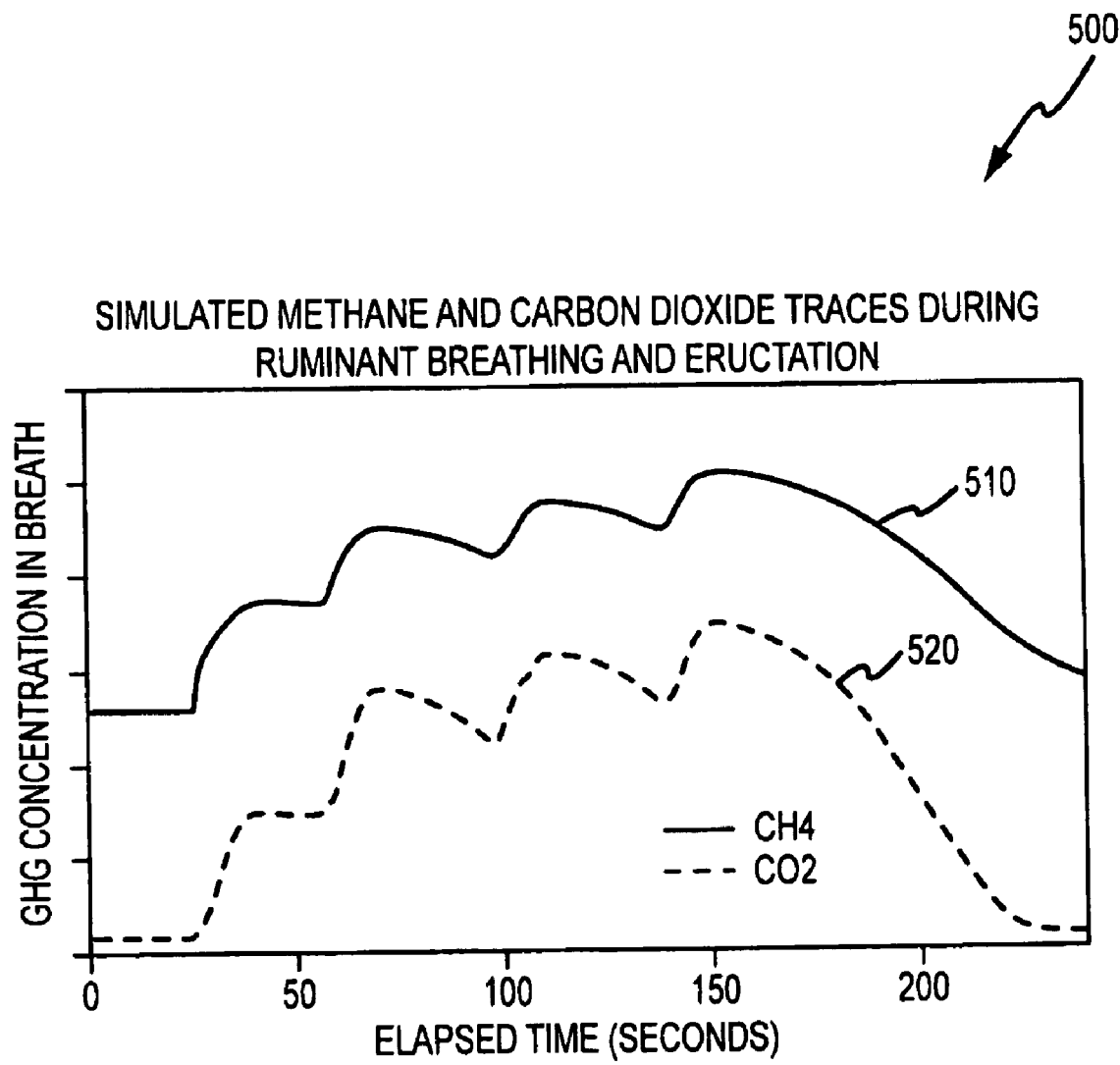
FIG. 5 is a graph illustrating a typical pattern of methane and carbon dioxide traces that may be measured within a manger/hood of a feed station in a GreenFeed system in accordance with an embodiment of the invention in a ruminant's breath (e.g., during an eructation cycle or the like)

In this way, absolute mass fluxes of methane and carbon dioxide can be measured or determined (by, for example, the data analyzing station 490). FIG. 5 illustrates a typical pattern 500 of ruminant animal breath and an eructation cycle that may be measured or monitored by the NDIR $CH_4$ and $CO_2$ analyzer 116 and/or determined by data processing software/modules of the data analyzing station 490 as part of process 400. Line 510 represents measured or determined concentrations of $CO_2$ in a ruminant's breath (as may be measured in a manger or hood 112 in a system 100) while line 520 represents measured or determined concentrations of $CH_4$ in the same ruminant's breath. 100401 When the animal removes its head from the GreenFeed system (or a hood 110), the system may in some embodiments be set to continuously monitor the air within the manger area (or hood 110) of the system to monitor the decay of methane and carbon dioxide concentrations to ambient levels due to mixing with the atmosphere (such as by operation of an analyzer 116 and data logger 118 as described in the method 400 and by processing of collected/monitored data from the animal as described for data analyzing station 490 and its processing modules).

For rangelands where many hundreds of animals could be present, a monitoring and emission control system may sometimes be set up to only allow selected individuals to have access to the GreenFeed monitoring system (or to only monitor and control emissions from such animals based on identification of this subset of the ruminants via ear tag/RFID or other animal identification). The nutrient treatment may then be delivered to all animals, with the system being used to collect data from a representative sampling of individual animals (e.g., the same ones used to set the nutrient treatment or a differing set). The results may then be extrapolated through numerical models to quantify the results for the whole herd. In this way, one unit could serve several hundred animals and not every animal would have to be sampled all of the time (but, they may be in other implementations). Alternately, if all animals are equipped with RFID tags, the system may be programmed to select individuals from among the entire herd for random or routine sampling.

In brief, systems according to embodiments may be described as useful for monitoring changes in relative emission rates. It can supply data to numerical models to estimate methane fluxes and to calculate GHG emission reductions that may then be converted to or used to determine carbon credits. The system may use an internal or an external tracer to measure mass fluxes of methane, carbon dioxide, and other metabolic gases. The system may be configured in many ways.

Figure 6A:
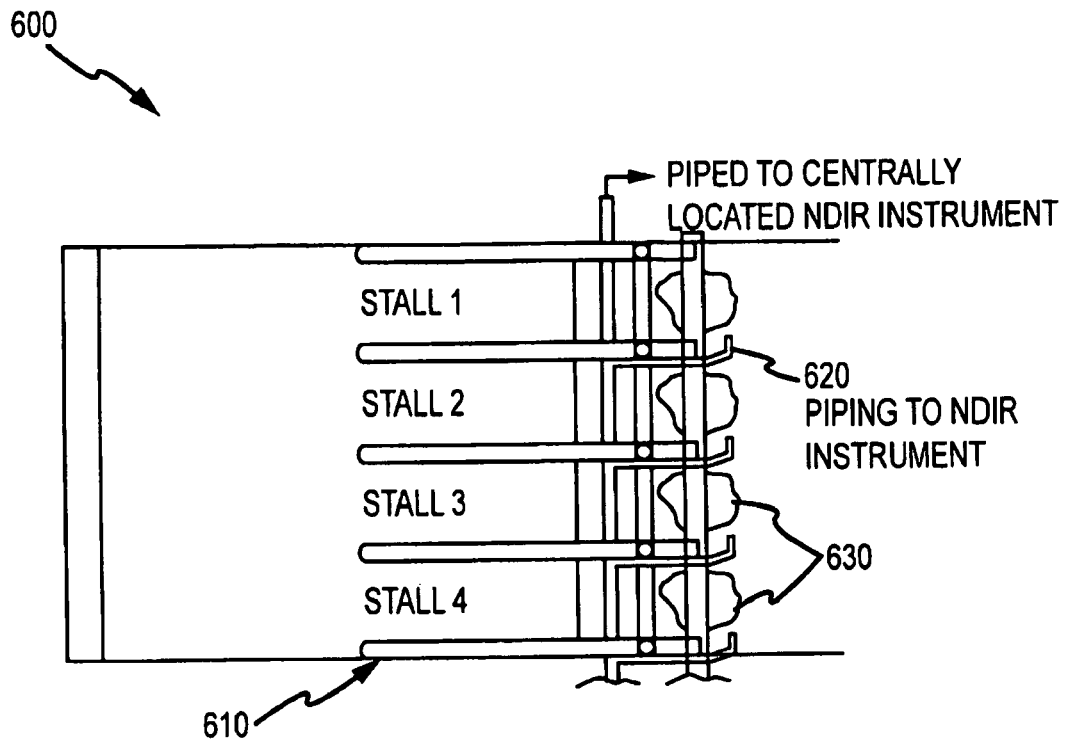
FIGS. 6A and 6B illustrate a portion of an embodiment of a GreenFeed system using a tie stall configuration to monitor and control GHG emissions of ruminants.
Figure 6B:
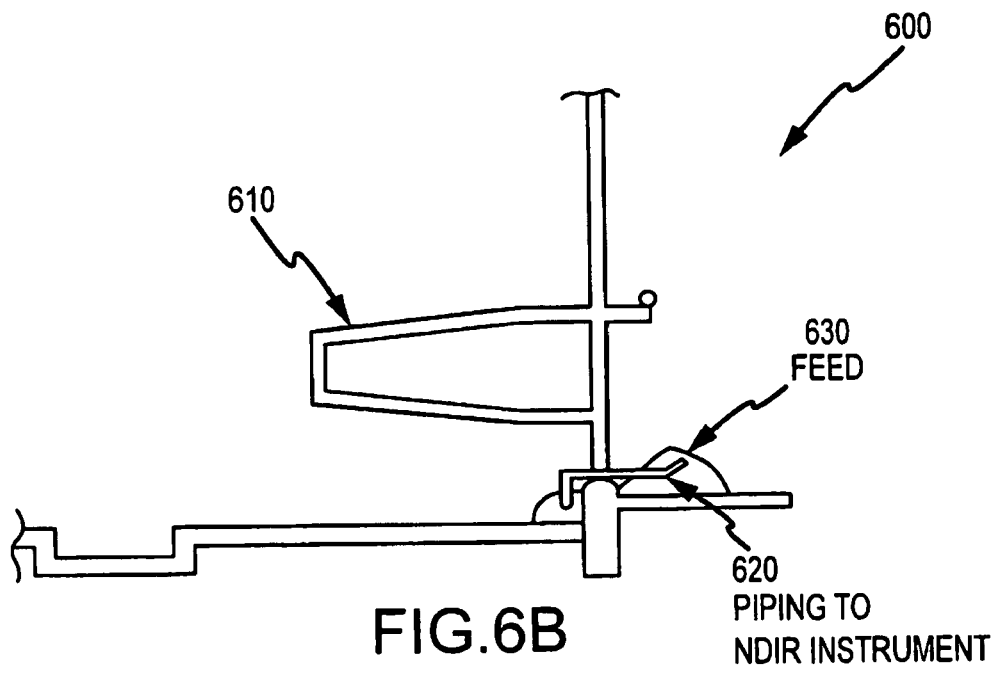

For example, as shown in FIGS. 6A and 6B (top and side views), a GreenFeed system 600 may be used in a group setting such as in a milking parlor or barn to measure all individuals at once. For example, the system 600 may be incorporated into headstalls 610 or other devices used to restrict animal movement. The system 600 includes piping 620 to move or transfer breath/gas samples from a feeding area (which may be hooded) in which the animal's head is located when provided feed 630 to one or more NDIR or similar analyzers/instruments. As discussed with reference to FIGS. 1-5, the feed 630 may be selectively modified in system 600 based on monitored levels of methane and/or carbon dioxide (as detected by operation of a $CO_2/CH_4$ analyzer and/or a data analyzing station and its running software modules) and/or be supplemented with select nutrients to reduce GHG production/emission.

In other embodiments (not shown), the monitoring and/or supplement dispensing portions of the inventive system are added to automated robotic milking machines to monitor methane and carbon dioxide ratios while animals are being milked. As will be appreciated, the monitoring and control or GreenFeed systems may be used in nearly any setting where ruminants access food or water or otherwise place their heads in a certain position for an acceptable period of time to obtain breath monitoring measurements (e.g., the feed station of FIGS. 1-3 may be replaced by the stalls of FIGS. 6A and 6B, be replaced or used within an automated milking system in which ruminants are typically placed in a position for milking and are often concurrently fed or provided nutrients/supplements, and so on). Other places cattle and other ruminants may be forced to or willingly congregate (and which lend themselves as monitoring/nutrient dispensing stations) and where mixing of their breath in the atmosphere may include water founts or watering stations (that may be hooded or protected from winds and mixing as discussed above for the feed stations) and nutrient/salt lick-type stations, and the like. In other words, the terms "feeding station," "hood," and "manger" are intended to be construed broadly and may generally cover any device or arrangement in which a ruminant may place their head for a period of time and their breath may be monitored with at least some limitation on mixing with ambient air, and, at least in some cases, where nutrients/supplements may be dispensed to control or reduce GHG emissions.

One illustrative system in accordance with an embodiment of the present invention includes a comprehensive measurement and validation system for reduction of bovine methane emission. The system includes a methane ($CH_4$) measurement technology, e.g., one with the accuracy and reliability that may be used for generation of carbon credits, with one embodiment of the system including a triple-beam/dual gas (methane and carbon dioxide ($CO_2$)) infrared measurement detector. When incorporated into a nutrient block station, feed station, milking station/parlor, water fount, or similar implementation and, optionally, combined with a standardized emission credit determination system, the system for monitoring and controlling/reducing ruminant methane production provides a valuable tool for the reduction of methane emissions from bovine and other ruminant sources.

In operation of an embodiment of such a system, a ruminant's gaseous emissions are monitored, methane emissions are determined, and the ruminant's feed supply is adjusted or supplemented or the ruminant is otherwise treated to reduce methane emissions. In some cases, a non-dispersive infrared instrument monitors carbon dioxide and methane emitted by a ruminant. The information thus obtained is considered (e.g., processed by software running on a system computer or by a system processor) along with animal statistics available from a database in system data storage and/or from information associated with an RFID tag attached to the ruminant, which may include heritage information, e.g., whether the animal is weaned, its age, and the like. Based upon the emission information and the other information about the ruminant, one or more of a plurality of supplements and/or a particular amount of the one or more supplements is offered or dispensed to the ruminant.

In an exemplary but not limiting method, a ruminant presents itself at a feeding station at which carbon dioxide and methane emitted by the ruminant in its breath are measured. Other measurements may also be taken. Along with information obtained from memory such as a ruminant tracking/monitoring database or from receipt of signals containing information stored on the animals RFID ear tag, at least one determination is made about the production of methane by the animal. Additional determinations which may be made include identification of one or more supplements or a mixture of supplements and amount or amounts thereof to offer to the ruminant to reduce the determined methane emission which would be expected to subsequently occur, should the ruminant's diet not be modified.

A ruminant methane monitoring and control feed station (e.g., a GreenFeed system or GreenFeed station) may be constructed and instrumented to function in several modes. In one example, the feed station includes a hood located over the feed manger to restrict the effects of the wind and serve to isolate and concentrate the breath of an individual animal. In this case, the animal, such as a cow, inserts its head into an opening in the hood or feed manger. At that time, a RFID or other reader or sensor reads an ear tag to determine the age and type of animal. Based on this information, a specific nutrient mix may be released. In a more typical embodiment, the mixture is designed specifically to reduce the production of methane by the ruminant or to meet a goal level of such emissions (such as to achieve a particular weight gain). The determinations controlling the type and amount of nutrient are in some cases based on input from sensors mounted inside the feed station and on the ground in proximity to the feed station. Information collected from such sensors may include animal weight in order to determine animal weight gain, methane and carbon dioxide ratios to determine animal metabolic efficiency, and additional measurements as useful to document performance (e.g., performance with regard to methane emission reduction/control and/or with regard to more optimum weight gain or weight maintenance such as for a mature dairy cow) and, in some cases, to generate CERCs (Carbon Emission Reduction Credits.)

In another example, in addition to the measurement of methane and carbon dioxide ratios in the animal's breath, the insertion of the animal's head into a feed hood, stall, or feed station of the present invention triggers the release of a specific, controlled flow-rate tracer. The tracer, for example, may be an inert gas such as sulfur hexafluoride, butane, or other chemical compound that is measured with instrumentation installed in the feed station. The dilution of the tracer is used to correct methane and carbon dioxide measurements for the effects of atmospheric dilution. In this way, the flux of methane and carbon dioxide can be determined as well as the metabolic methane and carbon dioxide ratios.

In another example of the present invention, the animal's breath is used as a tracer of atmospheric dilution. Because the breath of a ruminant is saturated with water vapor and is released at very close to the same temperature as the internal body temperature of the animal, both water vapor and temperature (latent and sensible heat) can be measured. A solid-state or similar sensor can be used to measure temperature and humidity of ambient air and also to measure the temperature and humidity of the air that includes the animal's breath inside the GreenFeed manger, other at least partially enclosed space, or even an open space in some applications. Since the animal's breath is saturated with water vapor, the difference between the water vapor mixing ratio of ambient air and that of the air inside the manger of the GreenFeed system can be used in some implementations to monitor mixing of air inside the feed hood of the GreenFeed system. This measurement of mixing can then be used to calculate the dilution of the animal's metabolic gas emissions and, therefore, the fluxes of methane and carbon dioxide can be determined. Alternatively, fast measurements can be made using eddy correlation technology. A fast eddy co-variance flux instrument that measures latent and sensible heat flux can be incorporated into the instrument suite of the feed station, allowing the measurements to be used to calculate dilution due to mixing of the animal's breath with the air inside the feed hood. Dilution is calculated, and the fluxes of methane and carbon dioxide from the animal are measured and documented in addition to determinations of metabolic efficiency ratio (e.g., a ratio of methane to carbon dioxide).

In a further embodiment, a nutrient block feeder system (not shown but at similar in arrangement as the system 100 in FIGS. 1-3) can be deployed to monitor methane and carbon dioxide concentrations of tidal breath as well as the eructation of ruminant animals while they are in a pasture. The system looks similar to a hooded saltlick mounted on a short post. The nutrient block in some embodiments is surrounded on all but one side by a cover. The uncovered side has hole large enough for an animal to insert its head and access a nutrient block or container(s) of one or more nutrients. Mounted under the hood is an RFID tag reader for reading/receiving information about each animal from its RFID ear tag. The nutrient block station further includes a methane/carbon dioxide monitor, a data logger, and, optionally, a communication device (e.g., a Bluetooth transmitter, a cell phone with modem, or other wireless/wired communication device). The station sometimes contains a GPS chip to obtain and collect information about location of the unit and the time of day that it was accessed by the animal. The system may be powered by batteries such as those recharged by solar cells but other battery-based power sources or power sources may be utilized in the GreenFeed systems described herein.

In one method for monitoring and controlling/reducing methane production of a ruminant, when an animal approaches the nutrient block station, the system turns on for a specified time-period to monitor and document methane/carbon dioxide ratios, the animal's identification number, the time, and/or the location of the station. Based on information collected and obtained and determinations made based on the information by the system's software modules or programs, a supplement is made available (by computer-based control of feed/supplement dispensers) to the animal to control, reduce, or maintain methane emissions at a presently set or defined level, which may be stored in a database and associated with the animal's ID (which, in turn, may be stored on their RFID ear tag or accessible via an ID code on their ear tag). Normally, animals may consume one to two ounces of supplement per day. The amount of supplement consumed per animal may be controlled by the GreenFeed system by modifying the salt content of the supplement (e.g., releasing additional salt with the supplement, releasing a supplement with a higher salt component, or the like).

In some cases, the station is placed strategically in a field near a point of congregation such as a water source or water fount. A station may be used to serve up to 40 to 100 or more animals. The system may be loaded with a placebo mineral block to document the baseline methane emissions for the herd and the pasture. In this way, the mineral supplement may be added to document GHG reductions, so that each animal, as well as the whole herd, is monitored in a very cost-effective way. If more exact emission rates of methane and carbon dioxide are useful (instead of relative changes in efficiency), an optional tracer release system may be incorporated into an embodiment of the monitoring and control system. The tracer release system utilizes a third chemical species (e.g., butane or an inert fluorocarbon that would emit at a defined rate). The dilution of the tracer is then utilized to correct for limited atmospheric mixing, which occurs when the animal's head is "under the hood." This may, in some cases, not be necessary, however, since concentrations of methane and carbon dioxide under the hood will often be many times greater than ambient concentrations, and efficiency gains may be documented with the ratio of the two gases not the absolute emission rate. The data is then transmitted or linked to a computer in which a resident numerical or processing module can determine methane emission reductions and, optionally, convert those reductions into verifiable carbon credits.

In addition to the generation of high value GHG offsets, the system may serve as a livestock management tool. The methane/carbon dioxide ratios obtained provide valuable information about the condition of the animal and of the pasture. Methane and carbon dioxide concentrations under the hood of the mineral block monitoring system are expected to be fairly high, i.e., much above ambient, such that measurements should be relatively easy. If preferred, however, an embodiment of the system may use an OEM NDIR instrument. Since the station is automated with computer-based controls for collecting data, processing the data, and selectively dispensing feed/supplements, the monitoring costs per animal may be quite low. Because one station can be shared among many cattle or other ruminants, the cost per animal may also be relatively low.

Useful parameters to be evaluated for methane and $CO_2$ include a detection limit, a detection range, a response time, repeatability, and selectivity. To determine a detection limit and range, in one non-limiting example, methane concentrations of 100 ppm to 2% (well below the LEL) and $CO_2$ concentrations of 400 ppm (ambient background) to 5% are evaluated. Response times may be calculated by generating a response curve and analyzing the curve to determine the time for the detector to reach 90% of its peak value based on a step change in gas concentration. Repeatability of the detector is determined by exposing it to step changes between a specific concentration and a background without challenge gas multiple times. The standard deviations of the responses may be calculated to provide a quantitative measurement of repeatability. Detector selectivity is proven by exposures to other gases likely to be present. These gases primarily include alcohols from the animal's breath (in the sub-10 ppm range) and the water vapor in their breath. A potential interferent gas may be ammonia from animal waste.

Information from the detector and the tracking system is typically transmitted from the nutrient block station or other collection station to a central location where data may be collected from multiple stations. Wireless networking technology is used in some implementations, with some embodiments using a commercially available wireless communication solution or technology such as Bluetooth or 802.11g (WiFi). Each of these technologies has advantages and disadvantages, and the appropriate solution for a given application is highly dependent upon the details of a specific application. The 802.11g standard is relatively inexpensive due to its wide commercial use and acceptance. This standard uses direct sequence spread spectrum technology and is somewhat susceptible to RF noise and interference. The Bluetooth standard is also low cost and is less susceptible to RF noise and interference because it uses a frequency hopping spread spectrum technology. A preferred central data collection unit is a PC or similar computing devices with conventional and well-known data storage/memory devices.

In brief, use of the methane production monitoring and control techniques and devices described herein is expected to reduce the parasitic GHG emissions from livestock and increase grazing efficiency. Use of these systems and methods is further expected to have a desirable and even substantial economic potential. In addition to animal efficiency gains, actual methane emission reductions expected based on the wide range of literature values may produce GHG offsets worth from $1 to $20 (U.S. dollars) per animal per year depending on diet and animal genetics.

In some embodiments, a precision ruminant feeding and greenhouse gas performance monitoring system is provided that includes a plurality of individual feeding or GreenFeed systems, e.g., that may be spread about a field for access by a herd of ruminant such as sheep, cattle, dairy cows, undomesticated animals such as deer or elk, or other non-ruminant animals such as pigs and horses. Each station of the system may include: a feed/supplement delivery system and hopper; a feeding station; an RFID tag and reader system (e.g., an RFID panel reader for use with conventional RFID ear tags for cattle and other domesticated animals); a data logger and instrument controller; and a nondispersive infrared sensor (NDIR) or similar device for determining presence/quantities of methane and carbon dioxide (and other gases). Each grain/supplement delivery system and hopper may take a number of forms with one example being a metal or plastic hopper (e.g., with up to a 600 pound capacity or the like) combined with a feed delivery system/dispenser mechanism for selectively delivering feed and/or supplements. The hopper/delivery system may be an enclosed feeder station that is, for example, capable of delivering up to about 4 pounds or more of feed per second. The individual feeding stations or hoods fed by such a delivery system may take the form of one-piece molded poly feeders or the like with, for example but not limitation, a heavy steel base or other devices for substantially rigid mounting. In some cases, each feeding station with its hood and manger is able to hold about 50 pounds of feed and/or supplement.

The animal monitoring portion of the system may include components able to identify each animal (such as a tag attached to an ear with an RFID tag storing an ID associated with the animal, a tag with a readable number, a tag with a barcode, or the like) and may also include a temperature monitor such as one that may be mounted with the ID tag or separately on the animals ear (e.g., a thermistor with electronics, an antenna, and battery for sensing and transmitting the animals temperature information wirelessly to a receiver on or near the feeding station/feed delivery system in the GreenFeed system/station). The processor/controller used to run software modules for processing methane, carbon dioxide, animal data, and the like and for controlling the feed delivery system may take a number of forms to practice the invention and, in one case, is a Campbell Scientific Data Logger and Instrument Controller adapted to provide the functions/methods described herein (e.g., a CR1000 or the like available from Campbell Scientific, Inc.). Likewise, the analyzer used to obtain methane and carbon dioxide (and other gas) measurements may take numerous forms to practice the invention, with one embodiment using an NDIR analyzer (e.g., a Picarro G1301 $CO_2/CH_4/H_2O$ Analyzer or the like) that provides a real time, trace gas monitor able to measure carbon dioxide, methane, and water vapor with parts-per-billion (ppbv) sensitivity.

Figure 7A:
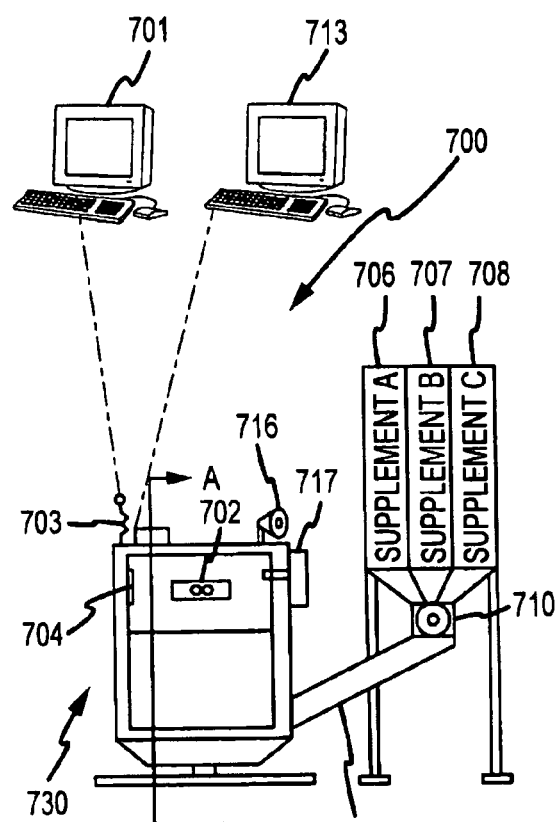
FIGS. 7A and 7B illustrate, similar to FIGS. 1-3, an embodiment of a system for monitoring and controlling ruminant methane production/emission (or another embodiment of a GreenFeed system)
Figure 7B:
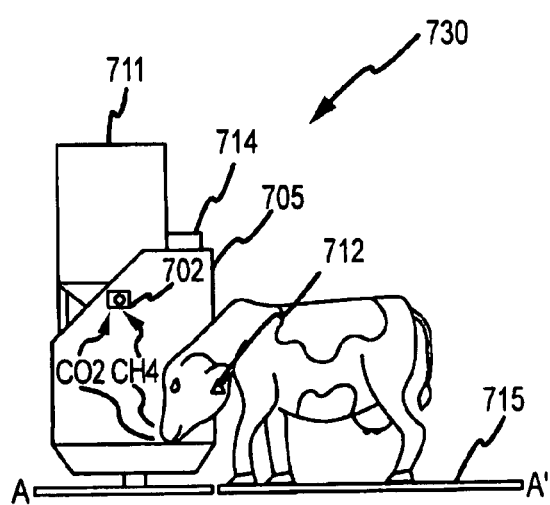

FIGS. 7A and 7B illustrate another embodiment of a GreenFeed system 700 that may be utilized to provide precision ruminant feeding to control GHG emissions and other parameters (such as ruminant weight gain and the like) and to provide GHG performance monitoring. The system 700 includes a number of the features or aspects of system 100 of FIGS. 1-3 and the description of system 100 may be applicable or relevant to system 700.

The system 700 includes a data analyzing station 701 (e.g., that may provide the functionality of data analyzing station 490 of FIG. 4). Data from a remote feeding station 730 may be transmitted via wireless communication to the data analysis station 701. The wireless data analyzing station 701, which may be a computer with a processor, I/O devices, a monitor, memory, and software (e.g., programs useful for providing the processing and other functions described herein), may operate to analyze and store the following data in local or remote memory or data storage: (i) ambient temperature; (ii) ambient pressure; (iii) relative humidity; (iv) wind speed; (v) time and date; (vi) $CH_4$ and $CO_2$ concentration over time (e.g., ambient and for individual animals); (vii) tracer gas type and amounts released; (viii) GreenCert or other carbon credit type information which may include, for example, data useful for a C-Lock Ruminant Module such as emissions baseline, change in emissions baseline, uncertainty, and incremental GHG reductions; (ix) animal identification through RFID technology; (x) animal body temperature; (xi) animal production statistics (e.g., beef statistics (e.g., current weight, gained or lost weight, rate of weight gain, estimate of future weight, feed efficiency compared to methane production, and $CO_2$ emissions per pound of gross animal weight) and dairy statistics (e.g., current milk production, increase or decrease of milk production, feed efficiency compared to methane production, and $CO_2$ emissions per unit of milk produced); (xii) animal genetics tracking (e.g., tracking and record of genetics bloodlines as it relates to methane production); (xiii) record of feed type and ration; and (xiv) formulation of future feed mixture and amount.

The system 700 may further include one or more nondispersive infrared sensors or other devices 702 useful for measuring $CO_2$ and $CH_4$ releases from a ruminant when their head is placed within the hood/manger of feeding station 730 (it should be noted that the feed station or its hood may be replaced by other stations such as milking stations in which a ruminant may insert their head or have their body/head in a particular position for a period of time allowing breath analysis). In one embodiment, the sensor(s) 702 may include a 3-bean optical design for $CH_4$, $CO_2$, and reference gas within a single light pipe or the like.

The system 700 may also include a wireless data communication device 703 mounted on or near the feed station 730. The communication device 703 may include a cellular digital modem or common technology to transmit stored or real time data from analyzer 702 and/or data logger 714. An ear tag scanner 704 such as a radio frequency identification (RFID) tag scanner may be placed or provide on or near the feed station 730, and the scanner 704 may scan and record individual animal data (in its own memory or data logger 714).

The feed station 730 may include an animal feeder such as a hooded manger or the like that is associated with hopper or gravity feed supplement bin 711. The bin 711 may have a number of separate compartments or bins for selectively providing a like number of nutrients and/or supplements to control GHG production/emission or achieve other goals such as weight gain. As shown, the hopper 711 includes three separate compartments with a first compartment 706 used to store/contain Supplement A (such as a first formulated supplement to reduce methane and/or increase animal production), a second compartment 707 used to store/contain Supplement B (such as a second formulated supplement to reduce methane and/or increase animal production), and a third compartment 708 used to store/contain Supplement C (such as a third formulated supplement to reduce methane and/or increase animal production).

The system 700 further includes a conveyer or gravity shoot 709 linking the bin 711 with the hood/manger 705 of feed station 730, and the gravity shoot/conveyor 709 supplies animal feeder 705 with feed supplement mix, which includes one or more of the supplements/nutrients from compartments 706, 707, 708. The system 700 includes a supplement measurement and mixing device 710 at the outlet of the supplement bin 711 (e.g., controlling output of each compartment 706, 707, 708 and its contained supplements), and the mixing device 710 mixes and measures individual animal ration from three or more store feed supplements, such as in response to control signals from the data analyzing station 701 (or software/hardware on the feed station 730 such as part of data logger 714 or the like). Each ruminant (or select ruminants within a herd) may be tagged (such as in the ear) with an individual animal radio-frequency identification tag 712, and the tag identifies individual animal to the system 700 (such as by reading by the tag scanner 704 that may provide the data to the logger 714 and/or the data analyzing station 701 for look up of the animal's ID, information, and the like and/or for storage of collected data corresponding to the animal's accessing the station 730). In some embodiments, the tag 712 also acts to monitor temperature of the animal, and this data may be read by the scanner 704.

In some embodiments, the system 700 may include a hardwired data analyzing station 713 in place of or to supplement station 701. Data from a remote feeding station may be transmitted via wireless or wired communication to the data analysis station 713. The hardwired data analyzing station 713, which may be a computer with a processor, I/O devices, a monitor, memory, and software (e.g., programs useful for providing the processing and other functions described herein), may operate to analyze and store the following data in local or remote memory or data storage: (i) ambient temperature; (ii) ambient pressure; (iii) relative humidity; (iv) wind speed; (v) time and date; (vi) $CH_4$ and $CO_2$ concentration over time (e.g., ambient and for individual animals); (vii) tracer gas type and amounts released; (viii) GreenCert or other carbon credit type information which may include, for example, data useful for a C-Lock Ruminant Module such as emissions baseline, change in emissions baseline, uncertainty, and incremental GHG reductions; (ix) animal identification through RFID technology; (x) animal body temperature; (xi) animal production statistics (e.g., beef statistics (e.g., current weight, gained or lost weight, rate of weight gain, estimate of future weight, feed efficiency compared to methane production, and $CO_2$ emissions per pound of gross animal weight) and dairy statistics (e.g., current milk production, increase or decrease of milk production, feed efficiency compared to methane production, and $CO_2$ emissions per unit of milk produced); (xii) animal genetics tracking (e.g., tracking and record of genetics bloodlines as it relates to methane production); (xiii) record of feed type and ration; and (xiv) formulation of future feed mixture and amount.

The system 700 may further include a data logger 714 on/near each of the feed stations 730 provided in the system 700 (e.g., the system 700 may include 2, 3, or more stations 730) or at another location in system 700. Each data logger 714 may function to record and store data such as: (i) ambient temperature; (ii) ambient pressure; (iii) relative humidity; (iv) wind speed; (v) time and date; (vi) $CH_4$ and $CO_2$ concentration over time: ambient and individual animals; (vii) tracer gas type and amounts released; (viii) animal identification through RFID technology; (ix) animal body temperature; (x)

animal production statistics (e.g., beef statistics (such as current weight, gained or lost weight, rate of weight gain, estimate of future weight, feed efficiency compared to methane production, and $CO_2$ emissions per pound of gross animal weight) and dairy statistics (such as current milk production, increase or decrease of milk production, feed efficiency compared to methane production, and $CO_2$ emissions per unit of milk produced); and (xi) record of feed type and ration.

In some embodiments, the system 700 may further include a scale or other weight determination device 715 to determine and record individual animal weight (or pass the information to the data logger 714 for storing in memory or to the station 701, 713 for storage or processing). The scale 715 may be used to record gross weight of individual animals located at the feeding station 730. Some embodiments of the system 700 may also include an audio/visual indicator 716 (on the animal feeder 705 or elsewhere). The indicator 716 may be operated by the stations 701, 713 or by other control mechanisms to signal animals for feeding time or other events. Further, some embodiments of the system 700 may include a tracer gas release apparatus 707 in or near the animal feeder or hood 705. The release apparatus 707 may function (in response to control signals from the station 701, 713, a local controller such as in the analyzer 702, or the like) to release a tracer gas as a point of reference in measuring $CH_4$ and $CO_2$ by the analyzer 702 and/or data analyzing station 701, 713.

Figure 8:
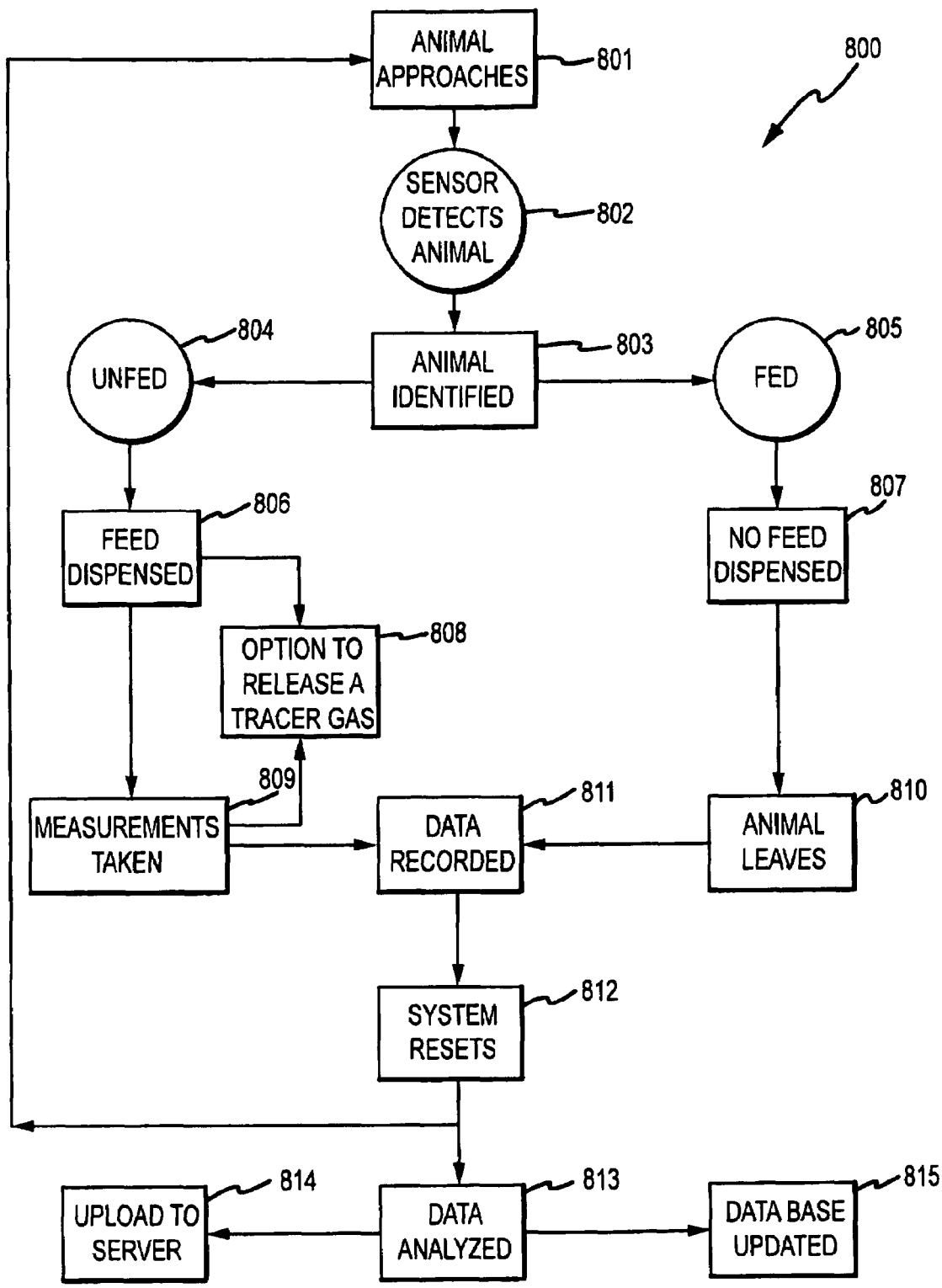
FIG. 8 illustrates a method of monitoring and controlling ruminant methane production and/or emission such as may be implemented, wholly or in part, by operation of the system shown in FIGS. 1-3, the system of FIGS. 6A and 6B, and/or the system of FIGS. 7A and 7B.

FIG. 8 illustrates a method 800 for monitoring and controlling GHG emissions (and other animal parameters in some applications) as may be practiced by operation of one or more of the GreenFeed systems described herein. At 801, an animal approaches a feed station or other monitoring location such as stall or portion of an automated or other milking station/parlor. At 802, a sensor may detect the presence of the animal (e.g., a scale, a tag reader, a motion detector, or other animal detection device), and, at 803, the animal is identified such as by use of an RFID tag reader to read an ear or other ID tag on the animal. A look up may be performed for the identified animal to determine whether the animal has been fed at 805 or unfed at 804. If fed, the feeding or other monitoring station is not operated to dispense food/nutrients as shown at 807, and the animal later leaves as shown at 810. Data may still be recorded at 811 regarding the animal and their access of the monitoring station (e.g., their temperature, their weight, and other animal monitoring information discussed herein).

If at 804 it is determined that the identified animal has not been fed within a particular time period, a feed station or the like is operated at 806 to dispense feed. The feed may be chosen based on a prior breath analysis for the animal to try to control GHG production/emission or to control animal production. The dispensed feed, for example, may include a particular mixture of two, three, or more feeds and/or supplements that have been determined by a data analyzing station as appropriate for the identified animal in controlling their GHG emissions (or achieving an animal production goal such as weight gain, milk production, or the like). At 808, a trace gas release mechanism may optionally be operated to release a particular quantity of a known trace gas or gases for use in analyzing GHG in the animal's breath (as discussed in detail above). At 809, the feeding station and its NDIR analyzer or other gas analyzing equipment is operated to take measurements of the contents of the animal's breath including GHG emissions.

At 811, the measured data (and other animal data) may be recorded in a local data logger and/or after transmission to a data analyzing station. At 812, the feeding station resets 812 and awaits another animal. At 813, the method 800 continues with the data monitored at the individual feed or other station being analyzed by software/hardware provided at a data analyzing station (or locally at the feed station or other station in some cases). In step 813, the amounts of $CH_4$ and $CO_2$ may be determined for the animal along with ratios useful for determining which supplements and supplement/nutrient ratios may be used to control GHG production/emission by the animal. At 814, the data may be uploaded to a server (e.g., the data analyzing station, a server in a network with the analyzing station, or the like) and at 815, the database storing GHG and other monitored/analyzed data for each animal is updated to reflect the most recent feeding and monitoring of the animal with the collected/analyzed data being linked to the animal's ID (e.g., a record may be maintained for each animal with fields for each type of tracked information).

With the above description in mind, numerous other embodiments and particular implementations will be readily understood by those skilled in the arts. For example, it will be understood that the measurement device may be attached to any place where an animal congregates and mixing is restricted such as a passage way or a water fountain. In some embodiments, the system and/or method may be adapted to support calculating the methane and carbon dioxide flux from the decreases in concentration after an animal moves away from the feeder. In such cases, for example, the decay in methane and carbon dioxide concentrations may be used to establish a dilution factor that may be applied to the ratios to correct them for mixing.

In some implementations, the differentiation of metabolic carbon dioxide from ruminant carbon dioxide is tracked/measured so that these two processes can be quantified and differentiated. For example, in practice, when an animal is present (e.g., near a feed station, a milking stall/station, or the like), carbon dioxide from her breath will begin to immediately increase as she respires. Methane and carbon dioxide will likely both spike when an eructation occurs and carbon dioxide will likely continue to increase between breaths. The slope of the increase, corrected for mixing, then gives the metabolic (muscle) carbon dioxide. The spike includes this but is dominated by rumen methane and carbon dioxide, and in some implementations, the metabolic component may be subtracted to more accurately determine the rumen component (e.g., this may not be presently reflected in the attached figures, but these figures may be modified to show that the carbon dioxide line continues to increase between the spikes, while the methane line will remain fairly flat). Note, that there is not much methane in metabolic air because methane is not soluble in blood and it therefore not much gets to the lungs.

In some particular embodiments, measurement of specific volatile organic compounds may be important or useful. For example, acetone may be utilized as a measure of acidosis. The inventor has made GCMS measurements of rumen gas and found it to contain a large number of volatile organics, any one of which could be an important marker for a specific process or condition and for which a dedicated sensor may be developed and/or included in the systems described herein. In some present embodiments or cases, a whole air sample is collected in an appropriate container made of Teflon™ film or of specially-passivated stainless steel may be used to collect a sample for later analysis in a research mode. However, to support commercial viability, a specific in-situ sensor may be developed and/or used. Further, it will be understood by those skilled in the arts that it may, at least in some applications, be useful to measure background methane and carbon dioxide in the air when the animal is not present in order to define the background concentrations present near the sensor. Such background measurements may allow these background concentrations to be subtracted from the elevated concentrations that occur due to the specific animal being measured to enhance accuracy of the described processes and systems.

What is claimed is:

1. A method of reducing methane emissions from a ruminant, comprising:
   providing a mechanism for dispensing feed to a ruminant, wherein the feed dispensing mechanism includes a gas analyzer;
   with the gas analyzer, measuring carbon dioxide and methane in emitted in breath of a ruminant accessing the feed dispensing mechanism; and
   operating a data analyzing station to determine, based on the measured carbon dioxide and methane, a supplement and an amount of the supplement to be presented in feed dispensed by the dispensing feed mechanism to a ruminant to reduce an amount of methane emitted.

2. The method of claim 1, further comprising with the data analyzing station, storing the determined supplement and the amount of the supplement in a memory device in a record associated with the ruminant accessing the feed dispensing mechanism.

3. The method of claim 2, further comprising operating the feed dispensing mechanism to provide feed including the supplement in the determined amount to the ruminant associated with the identification.

4. The method of claim 3, further comprising after the storing step, determining the ruminant associated with the identification is accessing the dispensing feed mechanism and retrieving information defining the supplement and the determined amount from the memory device using the identification, and using the retrieved information to perform the operating the feed dispensing mechanism step.

5. The method of claim 4, wherein the determining the ruminant associated with the identification is accessing the dispensing feed mechanism comprises operating a radio frequency ID (RFID) tag reader to read a tag on the ruminant to obtain the identification.

6. The method of claim 4, further comprising determining whether the ruminant associated with the identification has received a daily ration of the supplement and only when the daily ration has not been received, performing the operating the dispensing feed mechanism.

7. The method of claim 1, wherein the gas analyzer comprises a non-dispersive infrared instrument.

8. The method of claim 1, further comprising operating a trace gas release mechanism to discharge a volume of a trace gas proximate to the dispensed feed and wherein the volume of trace gas is used to calculate dilution from mixing with ambient air as part of performing the measuring of the carbon dioxide and the methane by the gas analyzer.

9. The method of claim 1, wherein the operating of the data analyzing station to determine the supplement and the amount of the supplement comprise determining a change in the ratio of the measured methane to the measured carbon dioxide relative to a prior methane to carbon dioxide ratio determination and using the determined change in the ratio to select the supplement and the amount.

10. The method of claim 1, further comprising determining a second supplement and an amount of the second supplement to provide in the dispensed feed with the supplement and the amount of the supplement to provide a mix of supplements in the dispensed feed.

11. The method of claim 10, wherein the dispensing feed mechanism comprises two storage compartments storing the supplement and second supplement and means for selectively dispensing the supplement and the second supplement concurrently from the storage compartments to provide the dispensed feed.

12. An apparatus for monitoring methane emissions from a ruminant, comprising:
    means for receiving the ruminant's head;
    a methane monitoring device positioned proximate to the means for receiving the head for monitoring methane in exhaled breath of the ruminant; and
    a container dispensing a supplement for consumption by the ruminant,
    wherein the container is operable to dispense the supplement in response to a determined level of the methane in the exhaled breath.

13. An apparatus for monitoring methane emissions from a ruminant, comprising:
    means for receiving the ruminant's head;
    a methane monitoring device positioned proximate to the means for receiving the head for monitoring methane in exhaled breath of the ruminant; and
    a container dispensing a supplement for consumption by the ruminant,
    wherein the supplement is adapted to reduce emission of methane in the exhaled breath of the ruminant.

14. An apparatus for monitoring methane emissions from a ruminant, comprising:
    means for receiving the ruminant's head;
    a methane monitoring device positioned proximate to the means for receiving the head for monitoring methane in exhaled breath of the ruminant; and
    a container dispensing a supplement for consumption by the ruminant,
    wherein the methane monitoring device further monitors a level of carbon dioxide in the exhaled breath, the apparatus further comprising a data analyzing station for determining a ratio of the methane and the carbon dioxide in the exhaled breath and for selecting the supplement based on the determined ratio.

15. An apparatus for monitoring methane emissions from a ruminant, comprising:
    means for receiving the ruminant's head;
    a methane monitoring device positioned proximate to the means for receiving the head for monitoring methane in exhaled breath of the ruminant;
    a container dispensing a supplement for consumption by the ruminant; and
    a device for detecting data about the ruminant including data stored on an RFID tag on the ruminant.

16. A method for monitoring and controlling methane production by a ruminant, comprising:
    determining a ruminant is proximate to a feeding station including determining an identifier for the ruminant;
    for a present feeding period, determining whether the identified ruminant has received a prescribed ration of nutritional supplement and feed;
    when the ruminant is determined to have not received the prescribed ration for the present feeding period, operating a supplement and feed dispenser in the feeding station to dispense the prescribed ration of the supplement and feed to a feeder;
    while the ruminant accesses the feeder to feed, measuring a level of methane and a level of carbon dioxide; and
    with a processing module run by a processor, modifying the prescribed ration stored in memory to include a differing type or amount of one or more dietary supplements in the prescribed ration of nutritional supplement and feed.

17. The method of claim 16, wherein the modified prescribed ration is used when the operating of the supplement and feed dispenser is repeated for the ruminant, whereby methane production by the ruminant is controlled.

18. The method of claim 16, wherein the differing type or amount of the dietary supplement is determined by the processing module based on a predefined methane production goal for the ruminant stored in the memory compared with the measured level of methane.

19. The method of claim 16, wherein the differing type or amount of the dietary supplement is determined by the processing module based on a determined ratio of the measured level of methane and the measured level of carbon dioxide.

20. The method of claim 19, further comprising measuring a level of water vapor while the ruminant is accessing the feeder and wherein the differing type or amount of the dietary supplement is determined by the processing module based on a determined ratio of the measured level of methane and the measured level of carbon dioxide further based on the measured level of water vapor.

21. The method of claim 16, wherein the measured level of methane and the measured level of carbon dioxide are used to determine a metabolic efficiency for the ruminant and wherein the metabolic efficiency is used to select differing type or amount of one or more dietary supplements in the prescribed ration of nutritional supplement and feed.

22. The method of claim 16, further comprising after the modifying of the prescribed ration dispensing a nutrient supplement based on the modified prescribed ration to the ruminant.

23. The method of claim 16, further comprising releasing a tracer gas within the feeder and measuring a level of the tracer gas, wherein the measuring of the levels of methane and carbon dioxide are based the level of the tracer gas, whereby dilution caused by mixing with ambient air is used in gas measurements.

24. A method for monitoring and controlling methane production by a ruminant, comprising:
when a ruminant accesses a feeder dispenser, reading data from a tag on the ruminant identifying the ruminant;
accessing a methane production monitoring database in memory with the identifying data to determine a nutritional supplement and an associated supplement quantity associated with the ruminant;
operating a dispenser to dispense the quantity of the nutritional supplement into the feed dispenser;
while the ruminant accesses the feed dispenser to feed, measuring a level of methane and a level of carbon dioxide; and
with a processing module run by a processor, determining a metabolic efficiency of the ruminant and modifying the nutritional supplement or the associated supplement quantity based on the metabolic efficiency to reduce methane production by the ruminant.

\* \* \* \* \*